United States Patent [19]
Habuka et al.

[11] Patent Number: 5,340,732
[45] Date of Patent: Aug. 23, 1994

[54] ANTIVIRAL PROTEIN

[75] Inventors: Noriyuki Habuka; Masashi Miyano; Takashi Matsumoto; Masana Noma, all of Yokohama, Japan

[73] Assignee: Japan Tobacco, Inc., Tokyo, Japan

[21] Appl. No.: 854,845

[22] Filed: Mar. 20, 1992

[30] Foreign Application Priority Data

Mar. 22, 1991 [JP] Japan .................. 3-083456

[51] Int. Cl.$^5$ .................. C12N 9/12; C12N 15/54; C12N 15/70
[52] U.S. Cl. .................. 435/193; 435/69.1; 435/71.3; 435/172.3; 435/252.3; 435/252.33; 435/320.1; 536/23.2; 935/10; 935/14; 935/29; 935/56; 935/72; 935/73
[58] Field of Search .................. 435/193, 71.3, 69.1, 435/172.3; 536/23.2; 935/10

[56] References Cited

FOREIGN PATENT DOCUMENTS 60-243100 12/1985 Japan .
2186988 7/1990 Japan .
376580 4/1991 Japan .

OTHER PUBLICATIONS

Pace (1990) Biotrend 2-4, pp. 105-110.
Habuka et al. (1990) *The Journal of Biol Chem.*, 265(19)10988-92.
Habuka et al. (1989) *The Journal of Biol. Chem.*, 264(12)6629-37.
Matsumura et al. (1989) Nature 342(16):291-293.
Matsumura et al. (1989) *Proc. Natl. Acad. Sci. USA* 86:6562-6566.
K. Hamaguchi (1991) *Biochemistry* 1, pp. 1-13.
Habuka et al. (1991) J. Mol. Biol., 221:737-743.
Habuka et al. (1991) *The Journal of Biol. Chem.*, 266(35):23558-60.
Olsnes et al. (1982) Molecular Aspects of Cellular Regulation 2(3):53-105.
C. N. Pace (1990) Tibs Trends in Biochemical Sciences, 15:14-17.

*Primary Examiner*—Robert A. Wax
*Assistant Examiner*—Rebecca Prouty
*Attorney, Agent, or Firm*—Birch, Stewart, Kolasch & Birch

[57] ABSTRACT

An antiviral protein having an amino acid sequence represented by sequence No. 8 of a Sequence Listing is disclosed. The protein is obtained such that cysteine residues in the basic protein (MAP) obtained from *Mirabilis jalapa* and having antiviral activity are substituted with serine residues. More specifically, a MAP gene in which codons encoding cysteines are substituted with codons encoding serines is prepared, and this gene is integrated in a MAP secretion vector. This vector is introduced into a host to express the gene, thereby obtaining the antiviral protein. This protein retains MAP advantages as a toxic protein and has higher protein synthesis inhibition activity than that of MAP, and almost equal to that of a lysine A chain.

2 Claims, 12 Drawing Sheets

```
                                                       ─── BLOCK I ───
       10         20         30         40         50         60
GCGCCTACTTC TAGAAACCAT CGCTTCTCTG GACCTGAACA ACCCGACCAC CTACCTGTCT
CGCGGATGAG ATCTTTGGTA GCGAAGAGAC CTGGACTTGT TGGGCTGGTG GATGGACAGA
                XbaI
       70         80         90        100        110        120
TTCATAACGA ATATCCGTAC GAAAGTCGCA GACAAAACCG AACAGTGTAC CATCCAGAAA
AAGTATTGCT TATAGGCATG CTTTCAGCGT CTGTTTTGGC TTGTCACATG GTAGGTCTTT
                   SplI
─── BLOCK II ───
      130        140        150        160        170        180
ATCTCTAAAA CCTTCACCCA GCGTTACTCT TACATAGACT TGATCGTGAG CTCGACGCAG
TAGAGATTTT GGAAGTGGGT CGCAATGAGA ATGTATCTGA ACTAGCACTC GAGCTGCGTC
                                                      SacI
      190        200        210        220        230        240
AAAATCACCC TAGCTATCGA CATGGCTGAC CTGTACGTTC TGGGTTACTC TGACATCGCT
TTTTAGTGGG ATCGATAGCT GTACCGACTG GACATGCAAG ACCCAATGAG ACTGTAGCGA
                                  ─── BLOCK III ───
      250        260        270        280        290        300
AATAACAAGG GTCGTGCTTT CTTCTTCAAA GACGTGACTG AGGCTGTTGC GAACAATTTC
TTATTGTTCC CAGCACGAAA GAAGAAGTTT CTGCACTGAC TCCGACAACG CTTGTTAAAG
                                            ─── BLOCK IV ───
      310        320        330        340        350        360
TTCCCGGGAG CTACAGGTAC TAATCGTATC AAATTAACCT TTACAGGTTC TTATGGCGAT
AAGGGCCCTC GATGTCCATG ATTAGCATAG TTTAATTGGA AATGTCCAAG AATACCGCTA
       XcyI
      370        380        390        400        410        420
CTCGAGAAAA ACGGCGGACT ACGTAAGGAC AATCCCCTAG GTATCTTCCG TCTGGAAAAC
GAGCTCTTTT TGCCGCCTGA TGCATTCCTG TTAGGGGATC CATAGAAGGC AGACCTTTTG
                                          AvrII
                                ─── BLOCK V ───
      430        440        450        460        470        480
TCGATAGTTA ACATTTATGG CAAAGCTGGT GACGTTAAAA AACAGGCTAA ATTCTTCTTA
AGCTATCAAT TGTAAATACC GTTTCGACCA CTGCAATTTT TTGTCCGATT TAAGAAGAAT 490        500        510        520        530        540
CTGGCTATCC AGATGGTTTC GGAGGCTGCG CGCTTTAAGT ATATCAGTGA CAAAATCCCG
GACCGATAGG TCTACCAAAG CCTCCGACGC GCGAAATTCA TATAGTCACT GTTTTAGGGC
                           BssHII
                                ─── BLOCK VI ───
      550        560        570        580        590        600
TCTGAAAAAT ACGAAGAAGT TACCGTTGAC GAATACATGA CCGCTCTGGA AAACAACTGG
AGACTTTTTA TGCTTCTTCA ATGGCAACTG CTTATGTACT GGCGAGACCT TTTGTTGACC
                                            ─── BLOCK VII ───
      610        620        630        640        650        660
GCTAAACTGT CTACGGCCGT ATACAACTCT AAGCCTTCTA CCACCACCGC TACCAAATGT
CGATTTGACA GATGCCGGCA TATGTTGAGA TTCGGAAGAT GGTGGTGGCG ATGGTTTACA
                  Eco52I
                                                    ─── BLOCK VIII ───
      670        680        690        700        710        720
CAGCTGGCTA CCTCTCCGGT TACCATCTCT CCGTGGATAT TCAAAACCGT CGAGGAAATC
GTCGACCGAT GGAGAGGCCA ATGGTAGAGA GGCACCTATA AGTTTTGGCA GCTCCTTTAG
                    BstEII
      730        740        750
AAACTGGTTA TGGGTCTGCT TAAGTCTTCT TAATAA
TTTGACCAAT ACCCAGACGA ATTCAGAAGA ATTATT
```

```
NdeI                                                      XbaI
MetLysLysThrAlaIleAlaIleAlaValAlaLeuAlaGlyPheAlaThrValAlaGlnAla AlaProThrLeu
TATGAAAAGACAGCTATCGCGATTGCAGTTGGCACTGGCTGGTTTCGCTACCGTAGCGCAGGCC GCGCCTACT
ACTTTTTCTGTCGATAGCGCTAACGTCAACCGTGACCGACCAAAGCGATGGCATCGCGTCCGG CGCGGATGAGAGATC
                           OmpA SIGNAL ↓   ↑ MAP
```

FIG. 3

```
EcoRI PstI SalI SD    NdeI          XbaI      BanIII  HindIII
AATTCCTGCAGGTCGACAGGAAACACATATGGCGCCTACTCTAGAAAATCGATAAA
     GGACGTCCAGCTGTCCTTTGTGTATACCGCGGATGAGATCTTTTAGCTATTTTCGA
```

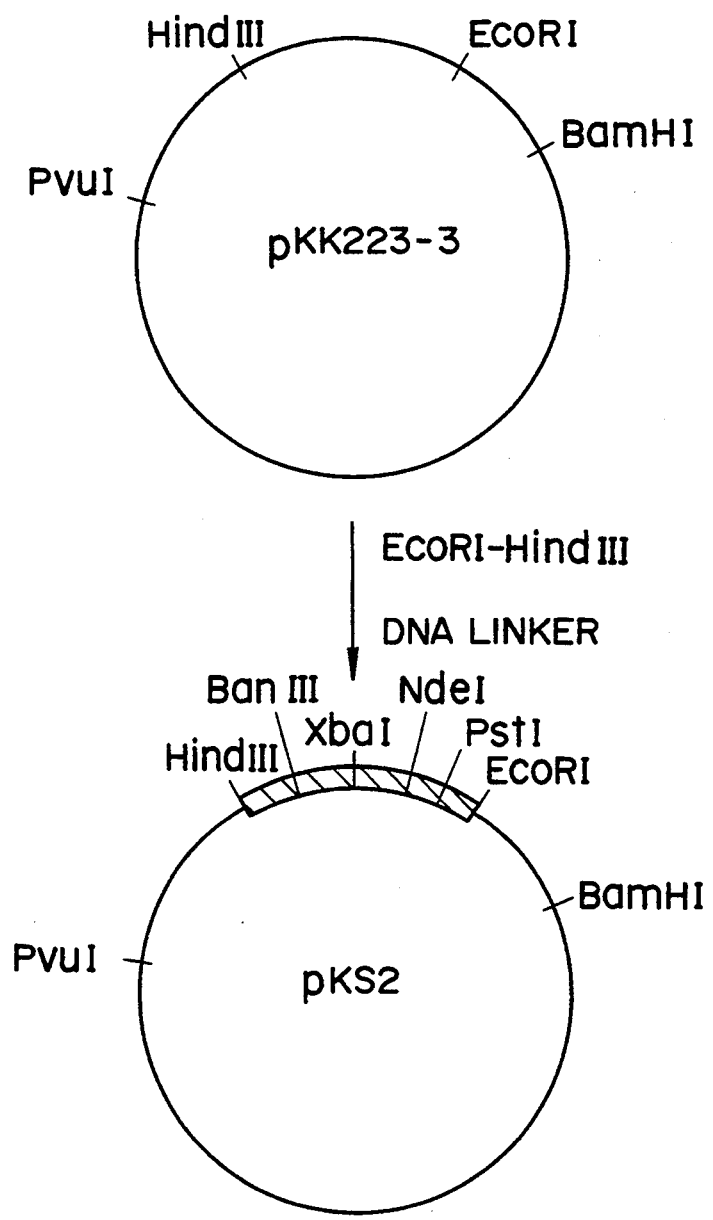
F I G. 4

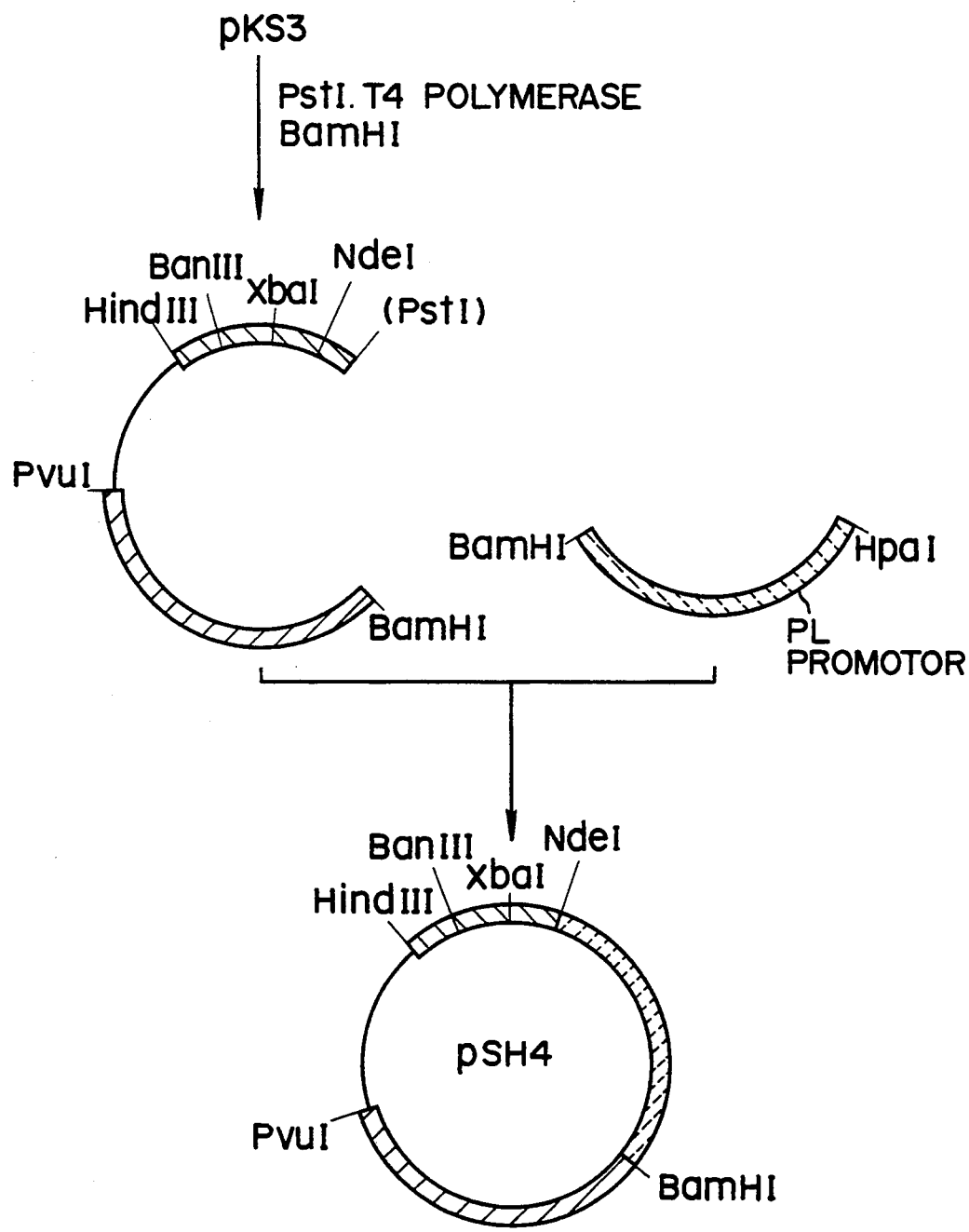
F I G. 6

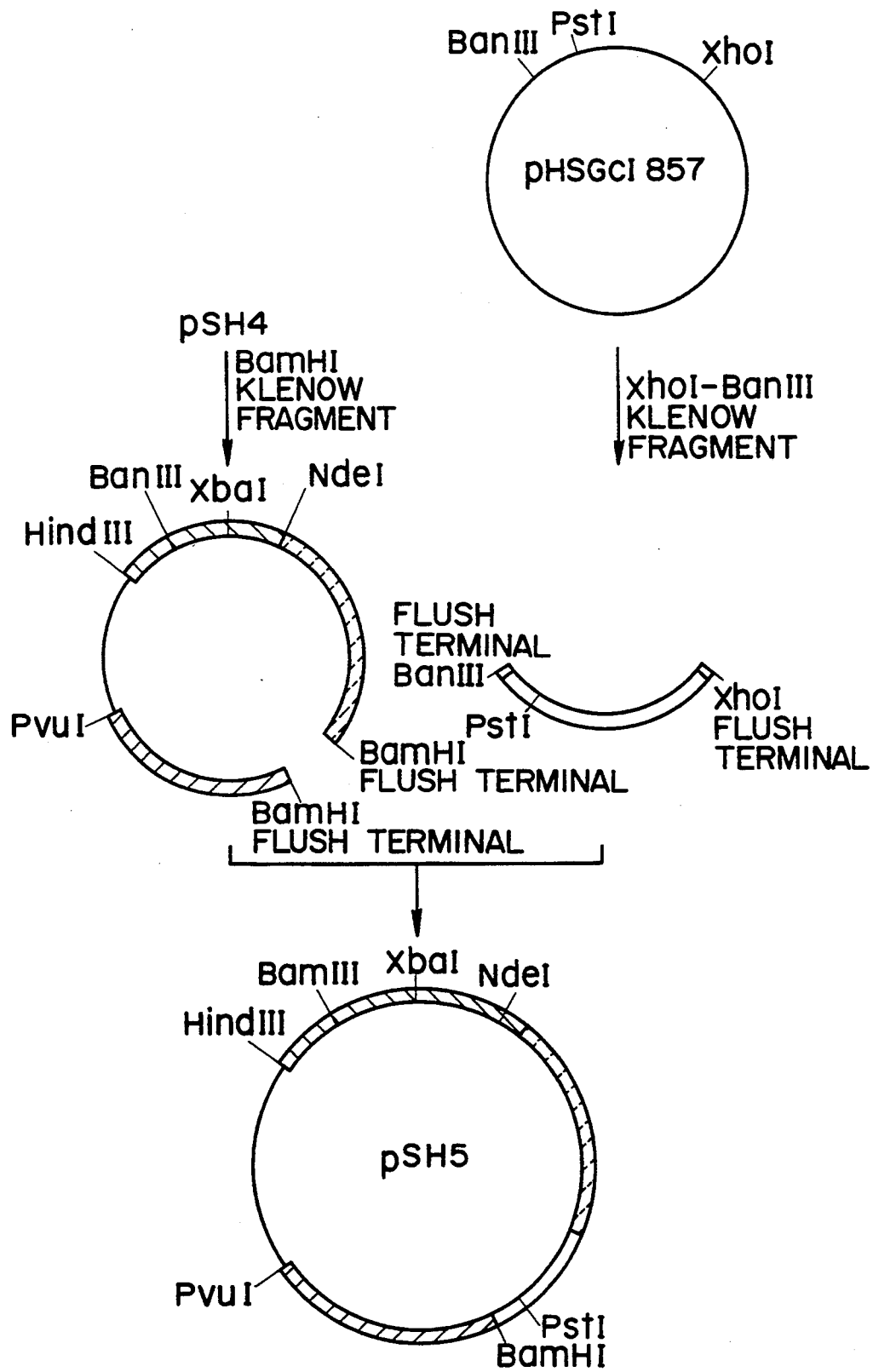
F I G. 7

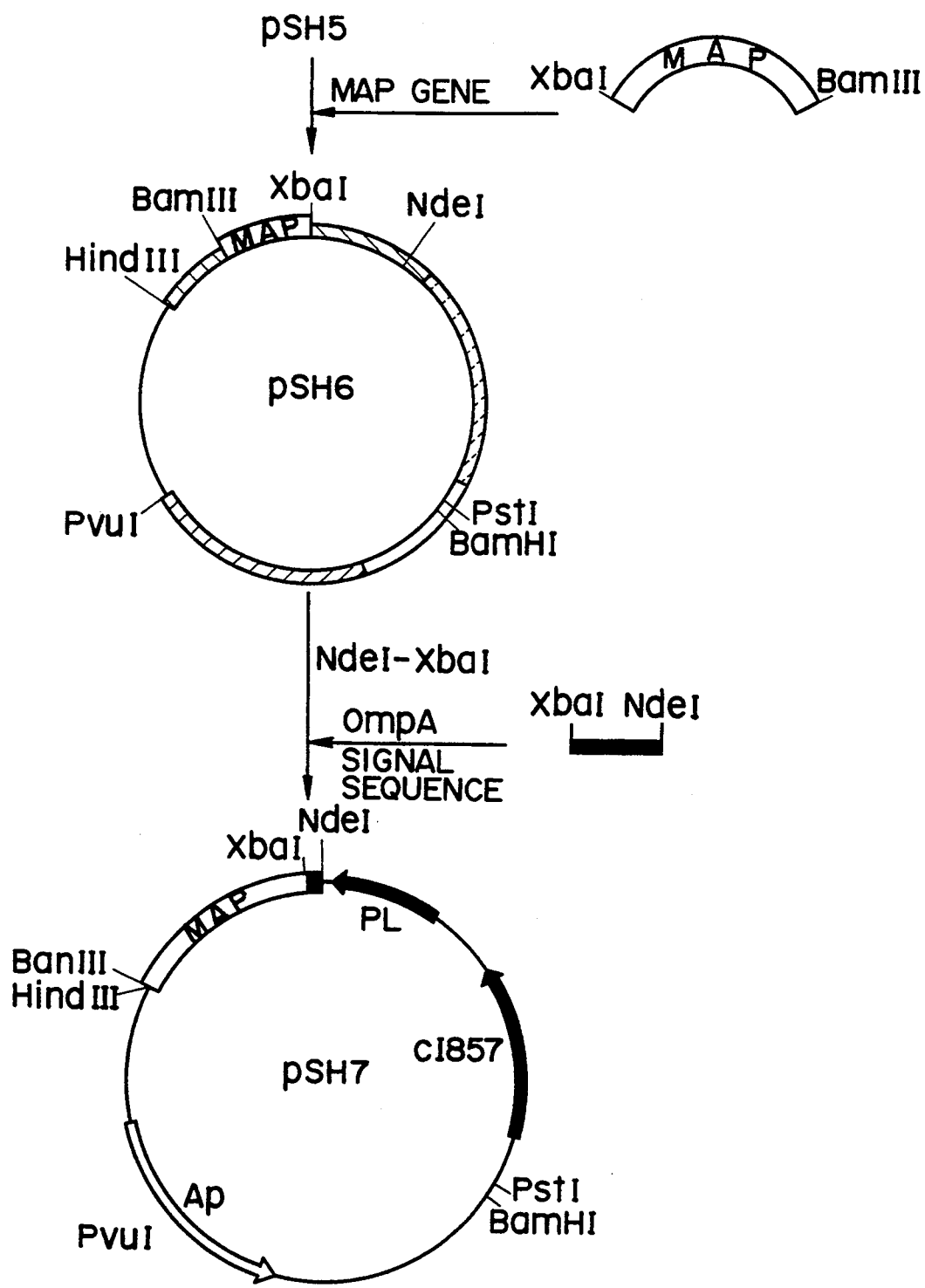
F I G. 8

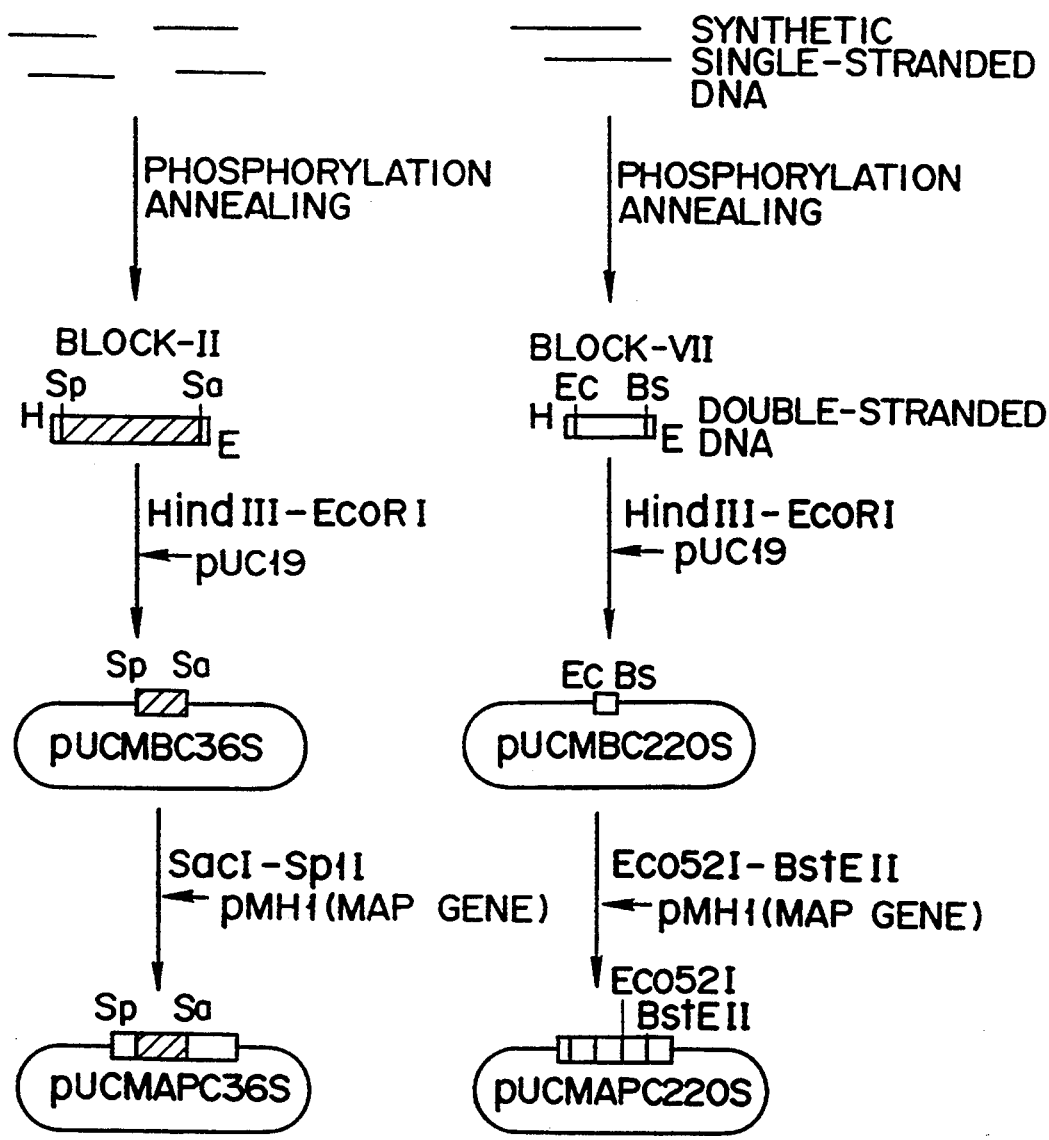
F I G. 9

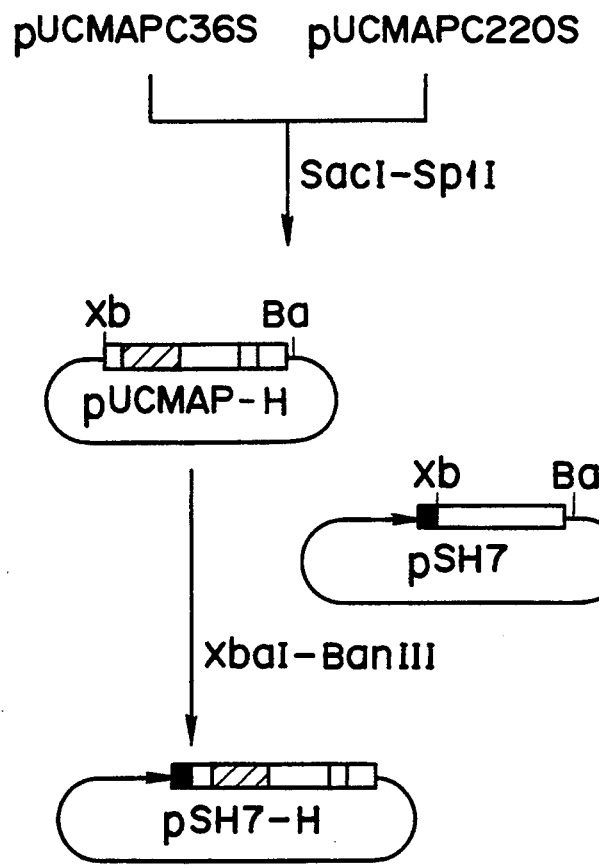
F I G. 10

HindIII SpII                                      SalI

AGCTTGG CGT ACG AAA GTC GCA GAC AAA ACC GAA CAG TCG ACC ATC

ACC GCA TGC TTT CAG CGT CTG TTT TGG CTT GTC AGC TGG TAG

Arg Thr Lys Val Ala Asp Lys Thr Glu Gln Ser Thr Ile

CAG AAA ATC TCT AAA ACC TTC ACC CAG CGT TAC TCT TAC ATA GAC

GTC TTT TAG AGA TTT TGG AAG TGG GTC GCA ATG AGA ATG TAT CTG

Gln Lys Ile Ser Lys Thr Phe Thr Gln Arg Tyr Ser Tyr Ile Asp

SacI    EcoRI

TTG ATC GTG AGC TC AAG

AAC TAG CAC TCG AG TTCTTAA

Leu Ile Val Ser

F I G. 11

HindIII     Eco52I

AGCTTGG CG GCC GTA TAC AAC TCT AAG CCT TCT ACC ACC ACC GCT

ACC GC CGG CAT ATG TTG AGA TTC GGA AGA TGG TGG TGG CGA

Ala Val Tyr Asn Ser Lys Pro Ser Thr Thr Thr Ala

BstEII    EcoRI

ACC AAA TCT CAA CTG GCT ACC TCT CCG GTT ACC AAG

TGG TTT AGA GTT GAC CGA TGG AGA GGC CAA TGG TTCTTAA

Thr Lys Ser Gln Leu Ala Thr Ser Pro Val Thr

F I G. 12

ANTIVIRAL PROTEIN

BACKGROUND OF THE INVENTION
1. Field of the Invention

The present invention relates to a Mirabilis Antiviral Protein (to be referred to as MAP hereinafter) variant and, more particularly, to a MAP variant whose inhibition activity in in vitro protein synthesis is improved as compared with that of natural MAP.

2. Description of the Related Art

The present inventors previously separated a novel basic protein from *Mirabilis jalapa* and found that this protein exhibited antiviral activity against a plurality of plant viruses. This protein was called MAP and was claimed in Published Examined Japanese Patent Application No. 63-61317. All amino acid sequences, synthesis of a gene based on the specified amino acid sequences, and construction of a system in *E. coli*, in which MAP is produced and secreted into the medium using this complete or full synthetic MAP gene were claimed in Published Unexamined Japanese Patent Application No. 2-186988 and Japanese Patent Application No. 1-210767.

The MAP is a type of ribosome inactivating protein (RIP) widely existing in plants and microorganisms, and exhibits an RNA N-glycosidase activity with high specificity for ribosomal RNA as a substrate. Ribosomes are inactivated by this activity, inhibiting protein synthesis, as is well known. Such protein synthesis inhibition activity is highly toxic in cells. In recent years, this toxicity has been utilized to develop immunotoxins having high selectivity, for example, by linking a ricin A chain, a type of RIP derived from *Ricinus communis*, to various antibodies. These immunotoxins are utilized, for example, in missile therapy.

This protein toxin possesses high antigenicity. There exists the possibility that an antibody against the toxin is produced in living bodies. Thus, long-term doses may adversely affect the living body. Therefore, proteins possessing various properties for use as toxic proteins are required.

Under these circumstances, the MAP is one of the most promising candidates as a toxin for an immunotoxin. The protein synthesis inhibition activity in a rabbit reticulocyte system has been shown to be only about 1/30 of the ricin A chain.

Protein engineering involving gene manipulation techniques has developed remarkably in recent years. In various applications, amino acid sequences of natural proteins are altered to produce proteins whose inherent activities are modified. It has been found in these applications that disulfide bonds (S-S bonds) in protein molecules are closely associated with the flexibility of the protein molecule, and that the activity can be greatly changed, depending on the presence or absence of S-S bonds (Matsumura et. al., *Nature* 342, pp. 291-293 (1989); Matsumura et. al., *Proc. Natl. Acad. Sci. USA* 87, pp. 6562-6566 (1989); Kozo Hamaguchi, Biochemistry 1, pp. 1-13 (1991); and Pace, *Biotrend* 2-4, pp. 105-110 (1990)).

When the foregoing is taken into consideration, the production of proteins possessing greater activity and, more particularly, possessing greater protein synthesis inhibition activity is expected by utilizing MAP genes.

SUMMARY OF THE INVENTION

It is an object of the present invention to provide a protein having high protein synthesis inhibition activity and, more particularly, a protein having higher protein synthesis inhibition activity than that of MAP.

The inventors have conducted extensive studies to achieve the above object, and have discovered a MAP variant having a higher protein synthesis inhibition activity than that of MAP by changing two cysteine residues associated with an S-S bond of the MAP into serine residues. That is, the antiviral protein according to the present invention is a MAP variant having an amino acid sequence represented by SEQ ID No:8 in the Sequence Listing to be described later.

This MAP variant having no cysteine bond (to be referred to as MAP-H hereinafter) is produced by converting a codon encoding cysteine into a codon encoding serine in the MAP gene, inserting the resultant gene into a MAP secretion vector, and introducing this vector into a host such as *E. coli*.

The MAP gene is a gene encoding MAP. An amino acid and a codon specifying this amino acid are not generally set in a one-to-one correspondence. One to six types of codons specifying one amino acid are generally present. A large number of types of MAP genes are present, and a large number of types of recombinant genes in which codons encoding cysteines are substituted with codons encoding serines are accordingly present. When this recombinant gene is to be introduced into a host cell to produce an antiviral protein of the present invention, all the recombinant genes can be utilized. When a specific amino acid is taken into consideration, however, the frequency of use of several types of codons encoding specific amino acids can be unbalanced, depending on the species. Thus, when *E. coli* is the host, a gene having the base sequence represented by SEQ ID No:1 in the Sequence Listing is preferably employed.

Production of a MAP gene based on a MAP amino acid sequence is described in detail in Japanese Patent Application No. 63-93494. According to this method, a codon encoding cysteine is substituted with a codon encoding serine to obtain a total synthetic gene encoding the antiviral protein of the present invention. An *E. coli* transformant harboring a vector containing a total synthetic MAP gene produced by the above method has already been deposited in the Fermentation Research Institute (FRI) as deposit No. 9913. A total synthetic MAP gene can be extracted from this transformant, and only the codon encoding cysteine is substituted with a codon encoding serine to obtain a gene encoding the antiviral protein of the present invention.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate a presently preferred embodiment of the invention and, together with the general description given above and the detailed description of the preferred embodiment given below, serve to explain the principles of the invention.

FIG. 1 shows the base sequence of a synthetic gene encoding MAP;

FIG. 2 shows an OmpA signal sequence and the base sequence of the gene encoding the OmpA signal sequence, together with part of a MAP amino acid sequence and the base sequence of the gene encoding the MAP;

FIG. 3 shows the base sequence of a synthetic DNA linker;

FIG. 4 schematically illustrates step A in the Example of the present invention;

FIG. 6 schematically illustrates step C in the Example of the present invention;

FIG. 7 schematically illustrates step E in the Example of the present invention;

FIG. 8 schematically illustrates steps F and G in the Example of the present invention;

FIG. 9 schematically illustrates steps H and I in the Example of the present invention;

FIG. 10 schematically illustrates steps J and K in the Example of the present invention;

FIG. 11 shows the amino acid sequence of block II inserted in a MAP variant and the base sequence of a synthetic DNA fragment encoding this amino acid sequence according to the Example of the present invention;

FIG. 12 shows the amino acid sequence of block VII inserted in a MAP variant and the base sequence of a synthetic DNA fragment encoding this amino acid sequence according to the Example of the present invention;

DETAILED DESCRIPTION OF THE PREFERRED EMBODIMENT

Figure 5:
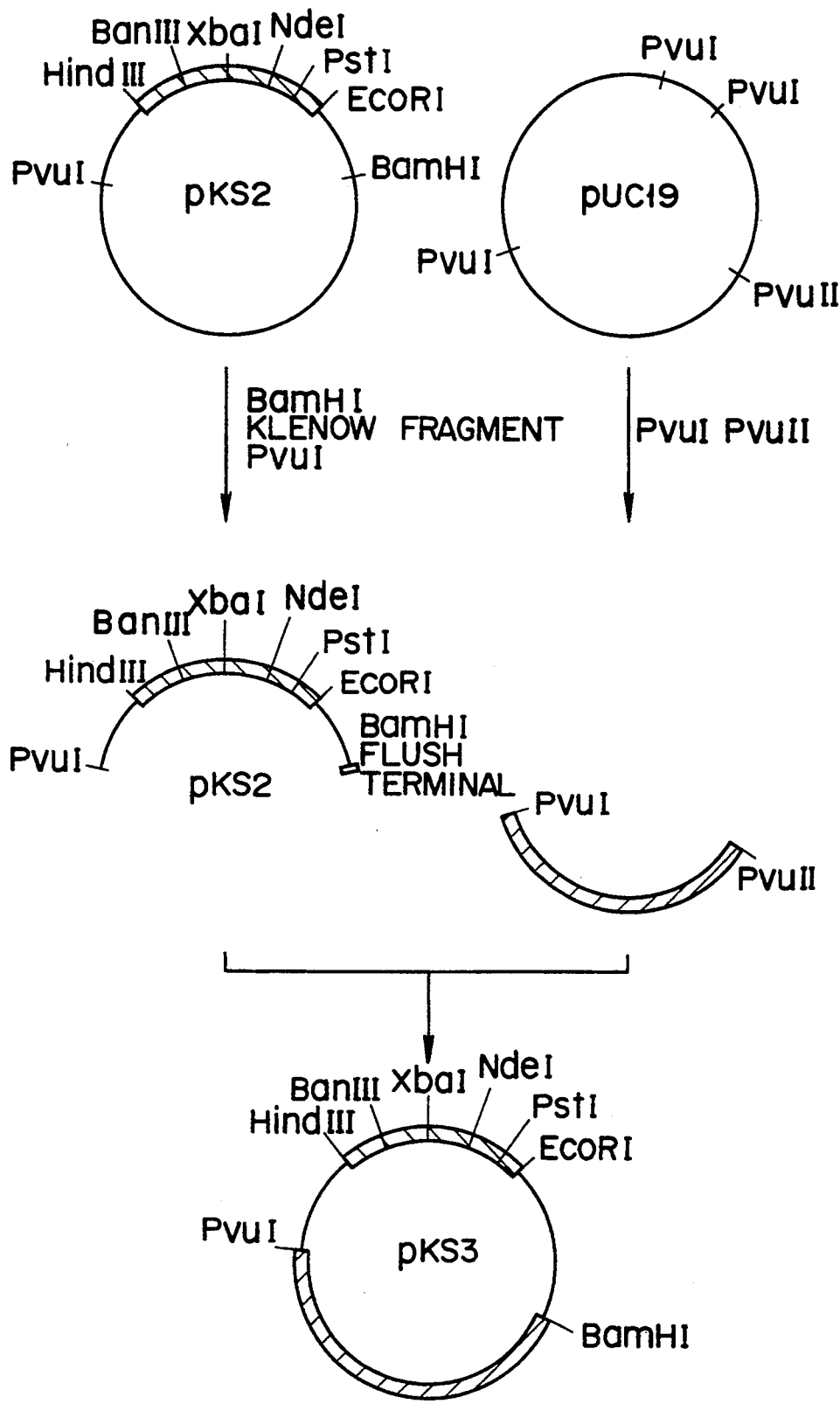
FIG. 5 schematically illustrates step B in the Example of the present invention.

A method of preparing an antiviral protein according to the present invention will be described in detail wherein a total MAP gene extracted from a deposited *E. coli* transformant is used.

I) Preparation of a MAP Gene Fragment in which A Codon encoding Cysteine is Substituted with A Codon encoding Serine A total synthetic MAP gene (SEQ ID NO:1) contained in the deposited *E. coli* transformant is constructed by linking the eight blocks I to VIII shown in FIG. 1. The blocks are linked at different restriction sites, respectively. A desired block can be obtained by using a specific restriction enzyme. Codons encoding two cysteine residues present in the MAP amino acid sequence are respectively present in blocks II and VII of this total synthetic MAP gene. In order to obtain a MAP gene encoding the MAP variant of the present invention, DNA fragments of these portions are newly synthesized, substituting a codon encoding cysteine with a codon encoding serine, and then the MAP gene is reconstructed using the new fragments in place of the fragments of blocks II and VII in the units of blocks.

For this purpose, a DNA fragment substituted with a target codon is synthesized and integrated in a plasmid. The plasmid containing this DNA fragment is cloned. At this time, it is desirable that the plasmid have the same base sequence as the original sequence, except that a restriction enzyme site is additionally inserted or deleted, and that the plasmid is cloned by use of the site as a marker. Note that synthesis is performed by using a commercially available DNA synthesizer, and purification is performed using HPLC. Known methods are used for phenol treatment and ethanol precipitation necessary for treating DNA, DNA digestion or cleavage by restriction enzymes, subsequent DNA recovery, the calcium treatment serving as the *E. coli* transformation method using the plasmid DNA, the alkaline-SDS method serving as the method of purifying DNA from *E. coli* transformants, and the dideoxy method serving as the sequence determination method for nucleic acids. For cloning, a presynthesized DNA is annealed such that the terminal ends of the resultant double-stranded DNA have EcoRI and HindIII sites, and the resultant double-stranded DNA is easily inserted into the plasmid, at which the same sites as the terminal ends of the resultant double-stranded DNA are present.

II) Insertion of Cloned DNA Fragments into the MAP Gene

Since the terminals of each block of the MAP gene form restriction enzyme sites, each cloned DNA fragment is cleaved at the corresponding site, and the cleaved fragment is then inserted into a total synthetic MAP gene. Insertion of each fragment is confirmed by the presence/absence of a newly inserted restriction enzyme site or a deleted restriction enzyme site. The inserted MAP gene is cleaved again with an appropriate restriction enzyme, and the cleaved portions are linked to each other to complete production of a MAP variant (i.e., MAP-H gene).

III) Production of an *E. coli* Expression Vector

A vector for introducing a foreign gene which is to be expressed in *E. coli* generally requires the following DNA sequences other than the gene to be introduced:

(a) a region for controlling transcription (operator).

(b) a region for promoting initiation of gene transcription (promoter).

Examples of promoters which are known to function in *E. coli* are the N25 promoter and the $P_L$ promoter, both of which are derived from coliphage, etc. The $P_L$ promoter is derived from *E. coli* lambda-phage, and is known to be repressed by a control protein which is called cI. The cI includes a temperature-sensitive variant, called $cI_{857}$, which represses the $P_L$ promoter at 30° C., like the cI, but which loses its repressing ability at 42° C., resulting in $P_L$ promoter activity. Accordingly, if an expression vector introduced in *E. coli* includes both the $P_L$ promoter and the $cI_{857}$ repressor gene, *E. coli* can be grown by culturing it at 30° C. such that the $P_L$ promoter is repressed. Also, the $P_L$ promoter can be turned on to initiate transcription of the gene by culturing *E. coli* at 42° C.

The $P_L$ promoter can be obtained by digesting lambda-phage DNA or the disclosed pPL-lambda plasmid with restriction enzymes BamHI and HpaI. The $cI_{887}$ repressor gene can be obtained by digesting DNA of lambda-phage variant ($cI_{857}$, Sam 7) with the restriction enzymes BglII and BanIII.

(c) a region for controlling the termination of transcription (terminator).

Examples of known terminators are the tLI terminator derived from coliphage, the rrnBT$_1$T$_2$ terminator derived from ribosome genes of E. coli, etc..

(d) a region for controlling the position of initiation of translation after transcription into mRNA (Shine-Dalgarno, SD sequence).

A sequence which is common to genes of E. coli can be used as an SD sequence.

(e) a methionine codon linked to the SD sequence for initiation of translation (ATG).

An expression vector derived from plasmid DNA can be constructed by deletion or insertion of a specific region from the plasmid DNA. The deletion and insertion can be performed by cleaving the plasmid at specific sites and combining the resultant fragments by means of an appropriate treatment. Specifically, appropriate utilization of synthetic DNA fragments enables restriction enzyme sites, an SD sequence, a gene encoding the amino acid sequence of a protein, etc. which are not present in the original plasmid DNA to be introduced.

For example, by making a DNA fragment including XbaI and BanIII sites that are not included in plasmid pKK223-3 and its complementary chain to combine with a cleavage fragment (a large fragment) which is obtained by digesting pKK223-3 with EcoRI and HindIII, the restriction enzyme sites for XbaI and BanIII can be introduced into pKK223-3. Additionally, by utilizing this pKK223-3 which includes the restriction enzyme sites XbaI and BanIII and a total synthetic MAP gene also having XbaI and BanIII sites at its 5'- and 3'-terminals, respectively, the total synthetic MAP gene can be introduced into plasmid pKK223-3. Further, an SD sequence and a codon encoding a methionine residue which is required for initiating gene transcription can also be introduced into said plasmid at this time. Moreover, since the restriction enzyme site of NdeI (CATATG) includes a methionine codon (ATG) therein, a gene encoding other proteins can be introduced through this site.

Required DNA fragments can be synthesized by a DNA synthesizer. An expression vector is formed by combining DNA fragments obtained from the DNA synthesizer, those obtained by restriction enzyme cleavage, and such a DNA fragment as needed, obtained by converting a cohesive end into a flush end utilizing T4 DNA polymerase, DNA polymerase Klenow fragment, etc. Each fragment can be combined using T4 DNA ligase or a commercially available ligation kit including the DNA ligase.

IV) Production of a MAP Secretion Vector

As described above, the total synthetic MAP gene having, e.g., the P$_L$ promotor and cI$_{857}$ gene obtained from the E. coli transformant (deposit No. 9913) deposited in the FRI, is integrated in an expression vector, and the expression vector is introduced into E. coli, thereby expressing the gene and hence mass-producing MAP in E. coli. In this case, the mass-produced MAP is stored in E. coli. This MAP affects the growth of E. coli and, thus, the production of MAP is limited. The mass-produced protein must be secreted outside E. coli.

OmpA is an outer membrane protein of E. coli and comprises a signal sequence (SE ID No:2) as shown in FIG. 2. The base sequence of a gene encoding this signal sequence is also shown in FIG. 2. This signal sequence functions to make OmpA secrete from E. coli. Therefore, by linking this signal sequence to the N-terminal end of other proteins, these proteins can be transferred outside from the inside of E. coli. For example, by linking the signal sequence shown in FIG. 2 to the N-terminal end of MAP, MAP can be secreted from E. coli.

Further, the gene encoding the signal sequence has the first methionine codon included in a part of said NdeI site, and thus a foreign gene can be introduced into an expression vector having an NdeI site downstream from a promoter.

FIG. 2 also shows a sequence of three amino acids of the MAP N-terminal region, and a DNA sequence corresponding thereto.

V) Insertion of the MAP-H Gene into the Secretion Vector

The MAP secretion vector obtained in step IV has a gene containing the OmpA signal sequence, and the MAP gene is inserted downstream thereof. The cleavage site of restriction enzyme XbaI is present in the N-terminal sequence of the MAP gene, and the BanIII site is present downstream of the C-terminal end. Therefore, the MAP-H gene obtained in step II is inserted using these two sites.

VI) Mass Production and Purification of MAP-H

If the MAP secretion vector used in step V has, e.g., the P$_L$ promotor and cI$_{857}$ coding for its control protein, expression of the MAP gene located downstream of the promotor is completely repressed at 30° C., and cI$_{857}$ is inactivated at 42° C. to immediately express the MAP gene, thereby producing the MAP. The signal sequence of E. coli outer membrane protein OmpA is inserted upstream of the MAP gene, so that the produced MAP is immediately secreted into the medium. A transformant containing the plasmid into which the MAP-H gene is inserted is cultured at a low temperature. When the concentration of the transformant reaches an appropriate value, the MAP-H gene is expressed by using the known temperature shift. The MAP-H is produced from E. coli, and is secreted into the medium. The resultant MAP-H is condensed as a precipitate by salting out with ammonium sulfate and then dialyzed. The dialyzed MAP-H is purified using Carboxymethyl Sepharose and Blue Sepharose column chromatography.

The MAP or MAP-H as a MAP variant is quantitatively evaluated by an ELISA (Enzyme-Linked Immunosorbent Assay) using an antiserum against MAP. In in vitro protein synthesis, i.e., translation, the RNA of tobacco mosaic virus is added as the mRNA in a protein synthesis system of a commercially available rabbit reticulocyte crude extract, and evaluation is performed using the content of labeled amino acid ($^{35}$S-methionine) present in the acid-insoluble polypeptide produced by the translation. At this time, an appropriate amount of MAP or MAP-H is added to the system to quantitatively evaluate its influence on this protein synthesis.

The present invention will be described in more detail by way of the following examples. The present invention, however, is not limited to the following examples. In order to readily understand the present invention, steps A, B, C, and E are illustrated in FIGS. 4, 5, 6, and 7, respectively; steps F and G are illustrated in FIG. 8; steps H and I are illustrated in FIG. 9; and steps J and K are illustrated in FIG. 10.

A) The Step of Inserting A Synthetic DNA Fragment into Plasmid pKK223-3

A DNA linker (SEQ ID No: 3) encoding restriction enzyme sites, an SD sequence, a methionine codon, and the N-terminal amino acid sequence of MAP shown in FIG. 3 was inserted into plasmid pKK223-3 extracted from *E. coli* (strain HB 101) transformed by a known method.

One microgram of pKK223-3 was incubated in High Salt Buffer (a mixture of 50 mM Tris-HCl, pH 7.5-100 mM NaCi-1 mM MgCl$_2$) containing 10 units each of restriction enzymes EcoRI and HindIII (manufactured by Nippon Gene Co, Ltd.) at 37° C. for one hour for digestion. The obtained solution was subjected to phenol-chloroform treatment and ethanol precipitation to collect the DNA. The phenol-chloroform treatment was as follows. Firstly, phenol was saturated with a mixture (hereinafter abbreviated as TE) of 10 mM Tris-HCl, pH 8.0, 1 mM ethylenediamine tetraacetic acid (EDTA). The equivalent volume of the resultant phenol solution was added to the obtained DNA solution for mixing, and the resultant mixture was centrifuged to collect the aqueous phase containing the DNA. Next, an equivalent volume of chloroform was added to this aqueous phase for further mixing, and the resultant mixture was centrifuged to collect the aqueous phase containing the DNA. Ethanol precipitation was performed as follows. Firstly, to the obtained solution containing the DNA, 5M sodium chloride, 1/20-fold volume, and ethanol, 2-fold volume, were added, and the resultant mixture was cooled at −70° C. for thirty minutes. Next, this solution was centrifuged at high speed to recover the obtained precipitate.

Two kinds of single-stranded synthetic DNA linkers, having the base sequences shown in FIG. 3, complementary to each other, were prepared by utilizing a DNA synthesizer (manufactured by Applied Biosystems Japan Company, 381A-type) according to the phosphoramidite method. One microgram of each obtained synthetic linker was incubated in 100 μl of a kinase solution (a mixture of 50 mM Tris-HCl, pH 7.6, 10 mM MgCl$_2$, 5 mM dithiothreitol, 0.1 mM spermidine, 0.1 mM EDTA, and 1 mM ATP) containing 10 units of T4 kinase (manufactured by Toyobo Co., Ltd.) at 37° C. for one hour to add phosphoric acid to the 5'-terminal end of the linkers. After that, the obtained single-stranded DNA was converted into double-stranded DNA by annealing. This annealing was performed by mixing the obtained reacted solutions, heating the resultant mixture at 60° C. for twenty minutes, and allowing it to stand at room temperature for twenty minutes. Next, the resultant solution was subjected to ethanol precipitation, and then the precipitate was dissolved in 10 μl of TE.

To 5 μl of the thus obtained solution containing double-stranded synthetic DNA, 2.5 μl (ca. 0.5 μg) of pKK223-3 cleavage product was added, and the mixture was ligated at 10° C. for two hours utilizing a ligation kit (manufactured by Takara Shuzo Co., Ltd.). After that, the resultant DNA was utilized to transform *E. coli* (strain HB101). From the obtained transformants, plasmid pKS2 was prepared. Plasmid pKS2 is the plasmid formed by inserting the synthetic DNA linker into plasmid pKK223-3.

B) The Step of Converting the Replication Origin of pKS2 to that of the plasmid pUC19 Type Two micrograms of plasmid pKS2 and restriction enzyme BamHI were incubated at 37° C. for one hour in 50 μl of High Salt Buffer for digestion. Next, the obtained solution was subjected to phenol-chloroform treatment and ethanol precipitation to collect the cleaved DNA. The obtained precipitate was added to 25 μl of Klenow solution (which is obtained by adding 0.1 mM of each co-factor dATP, dGTP, dCTP and TTP to a mixture of 50 mM Tris-HCl, pH 7.2, 10 mM MgSO$_4$, 0.1 mM dithiothreitol, and 50 μg/ml of bovine serum albumin) containing 2 units of Klenow fragment (manufactured by Toyobo Co., Ltd.), and the resultant solution was incubated at 22° C. for 30 minutes to convert the cohesive ends of the DNA to flush ends. After the reaction, the solution was heated at 70° C. for five minutes, followed by phenol-chloroform treatment and ethanol precipitation to collect the DNA. The collected DNA was further cleaved by dissolving it in 50 μl of High Salt Buffer containing 10 units of restriction enzyme PvuI (manufactured by Toyobo Co., Ltd.) and incubating at 37° C. for one hour. The cleaved DNA was collected by phenol-chloroform treatment, followed by ethanol precipitation.

Separately, 1 μg of plasmid pUC 19 (manufactured by Takara Syuzo Co., Ltd.) was incubated in 50 μl of High Salt Buffer containing 10 units each of restriction enzymes PvuI (manufactured by Toyobo Co., Ltd.) and PvuII (manufactured by Nippon Gene Ltd.) at 37° C. for two hours to cleave pUC19. The cleaved DNA fragments were collected by phenol-chloroform treatment, followed by ethanol precipitation.

The DNA fragment (larger fragment) derived from pKS2 and the DNA fragment derived from pUC19, both of which were obtained as described, were dissolved in 10 μl of TE, respectively. After that, 3.5 μl of each of the TE solutions were mixed, and the fragments were ligated at 10° C. for one hour utilizing a ligation kit (manufactured by Takara Shuzo Co., Ltd.). After that, the resultant DNA was utilized to transform *E. coli* (strain HB101). From the obtained transformants, plasmid pKS3 was prepared. pKS3 comprises the replication origin of pUC19 and the large fragment of pKS2 which are combined therein.

C) The Step of Inserting the P$_L$ Promotor into pKS3

Two micrograms of pKS3 were incubated in 50 μl of High Salt Buffer containing 10 units of restriction enzyme PstI (manufactured by Nippon Gene Co., Ltd.) at 37° C. for one hour for digestion. The cleaved DNA fragment was collected by phenol-chloroform treatment followed by ethanol precipitation. The collected DNA fragment was incubated in 20 μl of polymerase solution (which was obtained by adding 0.1 mM of each co-factor dATP, dGTP, dCTP and TTP to a mixture of 33 mM Tris-HCl, pH 7.9, 66 mM potassium phosphate, 10 mM magnesium acetate, 0.5 mM dithiothreitol, and 0.1 mg/ml of bovine serum albumin) containing 2.5 units of T4 DNA polymerase (manufactured by Toyobo Co., Ltd.) at 37° C. for five minutes to convert the cohesive end of the DNA fragment to a flush end. Next, 1 μl of 0.5M EDTA was added to the resultant solution, and the obtained mixture was subjected to phenol-chloroform treatment and further ethanol precipitation to collect the DNA. The collected DNA was incubated in 50 μl of High Salt Buffer containing 10 units of restriction enzyme BamHl (manufactured by Nippon Gene Co., Ltd.) at 37° C. for one hour for additional digestion.

Separately, 1 μg of pPL-lambda (manufactured by Pharmacia Co., Ltd.) was incubated in 50 μl of High Salt Buffer containing 10 units each of restriction enzymes BamHI and HpaI (both manufactured by Nippon Gene Co., Ltd.) at 37° C. for one hour for digestion. Next, the mixture was subjected to phenol-chloroform treatment and ethanol precipitation to collect the DNA fragment containing the $P_L$ promotor.

The DNA fragment derived from pKS3 and the DNA fragment containing the $P_L$ promoter were dissolved in 10 μl of TE, respectively. Next, 3.5 μl of each solution were mixed, and the DNA fragments therein were ligated utilizing a ligation kit (manufactured by Takara Syuzo Col, Ltd.). After that, the resultant DNA was utilized to transform E. coli (strain HB101). From the obtained transformants, plasmid pSH4 was prepared. pSH4 is the plasmid which was formed by inserting the $P_L$ promotor into pKS3.

D) The Step of Cleaving the cI857 Gene from Lambda-phage DNA

Two micrograms of lambda-phage (lambda, $cI_{857}$, Sam7) DNA (manufactured by Takara Syuzo Co., Ltd.) were incubated in 50 μl of High Salt Buffer containing 10 units each of restriction enzymes BglII (manufactured by Nippon Gene Co., Ltd.) and BanIII (manufactured by Toyobo Co., Ltd.) at 37° C. for two hours for digestion. The obtained DNA fragments were collected by phenolchloroform treatment followed by ethanol precipitation.

Meanwhile, 1 μg of plasmid pHSG397 (manufactured by Takara Syuzo Col, Ltd.) was incubated in 50 μl of High Salt Buffer containing 10 units each of restriction enzymes BamHI (Nippon Gene Co., Ltd.) and BanIII (manufactured by Toyobo Co., Ltd.) at 37° C. for one hour for digestion. Next, to the mixture, 2 μl (1 unit) of alkaline phosphatase (manufactured by Toyobo Co,, Ltd.) were added, and the resultant mixture was heated at 60° C. for 30 minutes for dephosphorylation at the 5'-terminal end of the DNA. After that, the DNA was collected by phenol-chloroform treatment and ethanol precipitation.

The lambda-phage DNA cleavage product and the pHSG 397 cleavage product which were thus obtained were each dissolved in 10 μl of TE. Next, 3.5 μl of each solution were mixed and the DNA cleavage products therein were ligated by reacting the mixture at 10° C. for two hours utilizing a ligation kit (manufactured by Takara Syuzo Co., Ltd.). The obtained DNA was utilized to transform E. coli (strain HB101), and plasmid DNA was purified from the obtained transformants. This plasmid DNA is pHSGcI857, formed by inserting the BglII-BanIII fragment of ca.1100 base pairs including $cI_{857}$ into pHSG397.

E) The Step of Inserting $cI_{857}$ into pSH4

Two micrograms of pHSGcI857 were incubated in 50 μl of High Salt Buffer containing 10 units each of restriction enzymes XhoI (manufactured by Nippon Gene Co., Ltd.) and BanIII (manufactured by Toyobo Co., Ltd.) at 37° C. for one hour for digestion. The cleaved DNA fragments were collected by phenol-chloroform treatment and ethanol precipitation. The collected DNA was incubated in 25 μl of Klenow solution containing two units of Klenow fragment at 22° C. for 30 minutes to convert the cohesive end of the DNA to a flush end. Next, the resultant solution was heated at 70° C. for five minutes and subjected to phenol-chloroform treatment and ethanol precipitation to collect the DNA.

On the other hand, 1 μg of pSH4 was incubated in 50 μl of High Salt Buffer containing 10 units of restriction enzyme BamH1 (manufactured by Nippon Gene Co., Ltd.) at 37° C. for one hour for digestion. The cleaved DNA was collected by phenol-chloroform treatment and ethanol precipitation. The collected DNA was incubated in 25 μl of Klenow solution containing 2 units of Klenow fragment at 22° C. for 30 minutes to convert the cohesive end of the DNA to a flush end. Next, the resultant solution was heated at 70° C. for five minutes, and subjected to phenol-chloroform treatment and ethanol precipitation to collect the resultant DNA.

The DNA fragment including $cI_{857}$ and the cleaved pSH4 fragments which were thus obtained were each dissolved in 10 μl of TE, respectively. Next, 3.5 μl of each solution were mixed and the DNA fragments were ligated by reacting the solution at 10° C. for two hours utilizing a ligation kit (manufactured by Takara Syuzo Co., Ltd.). The obtained DNA was utilized to transform E. coli (strain HB101), and plasmid DNA was purified from the obtained transformants. The obtained plasmid is pSH5 formed by inserting $cI_{857}$ into plasmid pSH4.

F) The Step of Inserting a Total Synthetic MAP Gene into pSH5

Two micrograms of pSH5 were incubated in 50 μl of High Salt Buffer containing 10 units each of restriction enzymes XbaI (manufactured by Nippon Gene Co., Ltd.) and BanIII (manufactured by Toyobo Co., Ltd.) at 37° C. for one hour for digestion The resultant solution was subjected to phenol-chloroform treatment and ethanol precipitation to collect the cleaved DNA.

Meanwhile, 2 μg of pMHI were digested and the cleaved DNA was collected in the same manner as for pSHS. pMHI is a synthetic plasmid formed by inserting a total synthetic MAP gene into the plasmid pUC19 and extracting it from the above-mentioned E. coli transformant (deposit No. 9913) deposited in the FIR.

The DNA fragment derived from pSH5 and the fragment from pMHI thus obtained were each dissolved in 10 μl of TE, respectively. Next, 3.5 μl of each solution were mixed and the DNA fragments therein were ligated by reacting the resultant mixture at 10° C. for one hour utilizing a ligation kit (manufactured by Takara Syuzo Co., Ltd.). The combined DNA was used to transform E. coli (strain N99cI+), and plasmid DNA was purified from the obtained transformants. This plasmid is pSH6 formed by inserting a fragment of the total synthetic MAP gene, which was obtained by cleaving with XbaI and BanIII, into the plasmid pHS5.

G) The Step of Inserting the Signal Sequence Gene of OmpA into pSH6

Each single-stranded DNA of complementary DNA fragments having the base sequences shown in FIG. 2 was synthesized according to the phosphoramidide method utilizing a DNA synthesizer (manufactured by Applied Biosystems Japan, type 381A). One microgram of each synthesized single-stranded DNA was incubated in 50 μl of said kinase solution containing 10 units of T4 kinase (manufactured by Toyobo Co., Ltd.) at 37° C. for one hour to phosphorylate the 5'-terminal end of the DNA. Each solution containing the phosphorylated single-stranded DNA was mixed, and the resultant solution was heated at 60° C. for 20 minutes and allowed to stand at room temperature for 20 minutes for annealing to obtain double-stranded DNA. The obtained double-stranded DNA was collected by ethanol precipitation and dissolved in 10 μl of TE.

On the other hand, 1 μg of the plasmid pSH6 was incubated in 50 μl of High Salt Buffer containing 10 units each of restriction enzymes NdeI and XbaI (both manufactured by Nippon Gene Co., Ltd.) at 37° C. for one hour for digestion. The cleaved DNA was collected by subjecting the reacted solution to phenol-chloroform treatment and ethanol precipitation. The collected DNA was further dissolved in 10 μl of TE.

3.5 μl of the TE solution containing the annealed synthetic DNA and 3.5 μl of the TE solution containing the cleaved pSH6 were mixed. The mixture was reacted at 10° C. for two hours by utilizing a ligation kit manufactured by Takara Syuzo Co., Ltd.) to combine the synthetic DNA and the cleaved DNA. The combined DNA was used to transform *E. coli* (strain N99cI+), and plasmid DNA was purified from the obtained transformants. This plasmid is plasmid pSH7 formed by inserting the OmpA signal sequence gene into pSH6.

H) The step of Cloning Blocks II and VII of the MAP Variant

DNA fragments having the base sequence (SEQ ID NO: 4) shown in FIG. 11 as four fragments and DNA fragments having the base sequence (SEQ ID NO: 6) shown in FIG. 12 as two fragments were synthesized by a DNA synthesizer (manufactured by Applied Biosystems Japan Company, type 381A), respectively. The synthesized products were DNA fragments of blocks II and VII of MAP-H genes. In this case, codons encoding serines in place of those encoding cysteines were used, being "TCG" and "TCT" respectively However, the codons are not limited to the above. Any codon may be used if it encodes serine.

One microgram of each fragment was incubated in 50 μl of a kinase solution containing 10 units of T4 kinase (manufactured by Toyobo Co., Ltd.) at 37° C. for one hour to phosphorylate its 5'-terminal end. The four kinds of incubated solutions, each containing different fragments, were mixed for block II, and the two kinds of incubated solutions, each containing different fragments, were mixed for block VII at 60° C. for 20 minutes, and the resultant solutions were left to stand for an hour at room temperature, thereby annealing complementary chains. Five μl of each resultant solution were added to 2.5 μl of a solution containing 0.1 μg of DNA obtained by cleaving plasmid pUC 19 with the restriction enzymes EcoRI and HindIII, treating with phenol and precipitating with ethanol, and were linked using a commercially available ligation kit (manufactured by Takara Shuzo Co., Ltd.). *E. coli* strain HB101 was transformed by the calcium method using the resultant plasmid, and the plasmid was purified from the resultant transformant by the alkaline-SDS method, thereby confirming that the synthesized DNA fragments were inserted. This confirmation was performed by DNA sequence determination according to the dideoxy method. Plasmid pUCMBC36S was obtained by insertion of fragments of block II, and plasmid pUCMBC220S was obtained by insertion of fragments of block VII.

I) The step of Inserting Block II and VII into A Complete Synthetic MAP Gene Block II was cleaved out from the resultant plasmid pUCMBC36S by the restriction enzymes SacI and SplI, and block VII was cleaved out from the resultant plasmid pUCMBC220S by the restriction enzymes Eco521 and BstEII. The cleaved blocks are inserted into the corresponding blocks of the complete synthetic MAP gene and thus substitute for them as follows. About 1 μg of each DNA cleaved by the corresponding restriction enzymes was subjected to phenol treatment and ethanol precipitation and was dissolved in 10 μl of a solution containing 10 mM Tris-HCl, pH 8.0 and 10 mM EDTA, respectively. 3.5 μl of each resultant solution were mixed, and the DNAs contained in each solution were ligated to each other using a ligation kit (manufactured by Takara Shuzo Co., Ltd.). The complete MAP gene was extracted from the *E. coli* transformant deposited in the FRI as deposit No. 9913. Using the resultant plasmid, i.e., a plasmid obtained by inserting a small fragment (i.e., block II or VII) cleaved out from the plasmid pUCMBC36S or pUCMBC220S into the complete synthetic MAP gene (pMH1), *E. coli* (strain HB101) was transformed by the calcium method. The plasmid was purified by the alkaline-SDS method from the resultant transformant. Insertion of each block was confirmed by the presence of a newly introduced SalI site for block II and by the absence of a deleted PvuI site for block VII. Plasmid pUCMAPC36S was obtained upon insertion of block II, and plasmid pUCMAPC220S was obtained upon insertion of block VII.

J) The step of producing a MAP Gene in which Two Codons encoding Cysteines are Substituted with Codons encoding Serines The plasmids pUCMAPC36S and pUCMAPC220S were cleaved by restriction enzymes SacI and SplI. The block II obtained by cleaving plasmid pUCMAPC36S was further cleaved by restriction enzyme ScaI so as not to convert it into the original plasmid. In a sample containing block VII obtained by cleaving plasmid pUCMAPC220S, alkaline phosphatase (manufactured by Toyobo Co., Ltd.) was added to the reacted solution to eliminate phosphoric acid at its 5'terminal end, so that the resultant DNA was not converted into the original plasmid unless other DNAs were inserted at positions cleaved by the restriction enzymes.

The respective plasmid cleavage products were subjected to phenol treatment and ethanol precipitation. Each sample was then dissolved in 10 μl of a solution containing 10 mM Tris-HCl, pH 8.0 and 10 mM EDTA, and 3.5 μl each of the resultant solutions were mixed to link them using a ligation kit (manufactured by Takara Shuzo Co., Ltd.) *E. coli* (strain MV1184) was transformed using the resultant plasmid in which both blocks II and VII were inserted. The plasmid was purified by the alkaline-SDS method from the resultant transformant. Insertion was confirmed by the presence/absence of the restriction enzyme site as in the previous step, thereby obtaining plasmid pUCMAP-Ho This plasmid contains the MAP-H gene having a base sequence represented as SEQ ID NO:1 in the Sequence Listing.

K) The step of Inserting the MAP-H Gene into MAP Secretion Expression Vector pSH7

The plasmid pUCMAP-H obtained in step J and the MAP expression secretion vector pSH7 obtained in step G were cleaved with restriction enzymes XbaI and BanIII, respectively, and were subjected to phenol treatment and ethanol precipitation. Each sample was dissolved in 10 μl of a solution containing 10 mM Tris- HCl, pH 8.0 and 10 mM EDTA, and 3.5 μl of each of the resultant solutions were mixed and linked using a ligation kit (manufactured by Takara Shuzo Co., Ltd.). *E. coli* (strain 99ci+) was transformed by the calcium method using the resultant plasmid. The plasmid was then purified from the resultant transformant by the alkaline-SDS method, thereby obtaining plasmid pSH7H, in which the MAP-H gene was inserted in pSH7. This *E. coli* transformant harboring plasmid pSH7H has been deposited in the FRI (deposit No.: FRI No. 12093).

L) The Step of Producing and Purifying A MAP Variant Having No Cysteine Bonds

Figure 13:
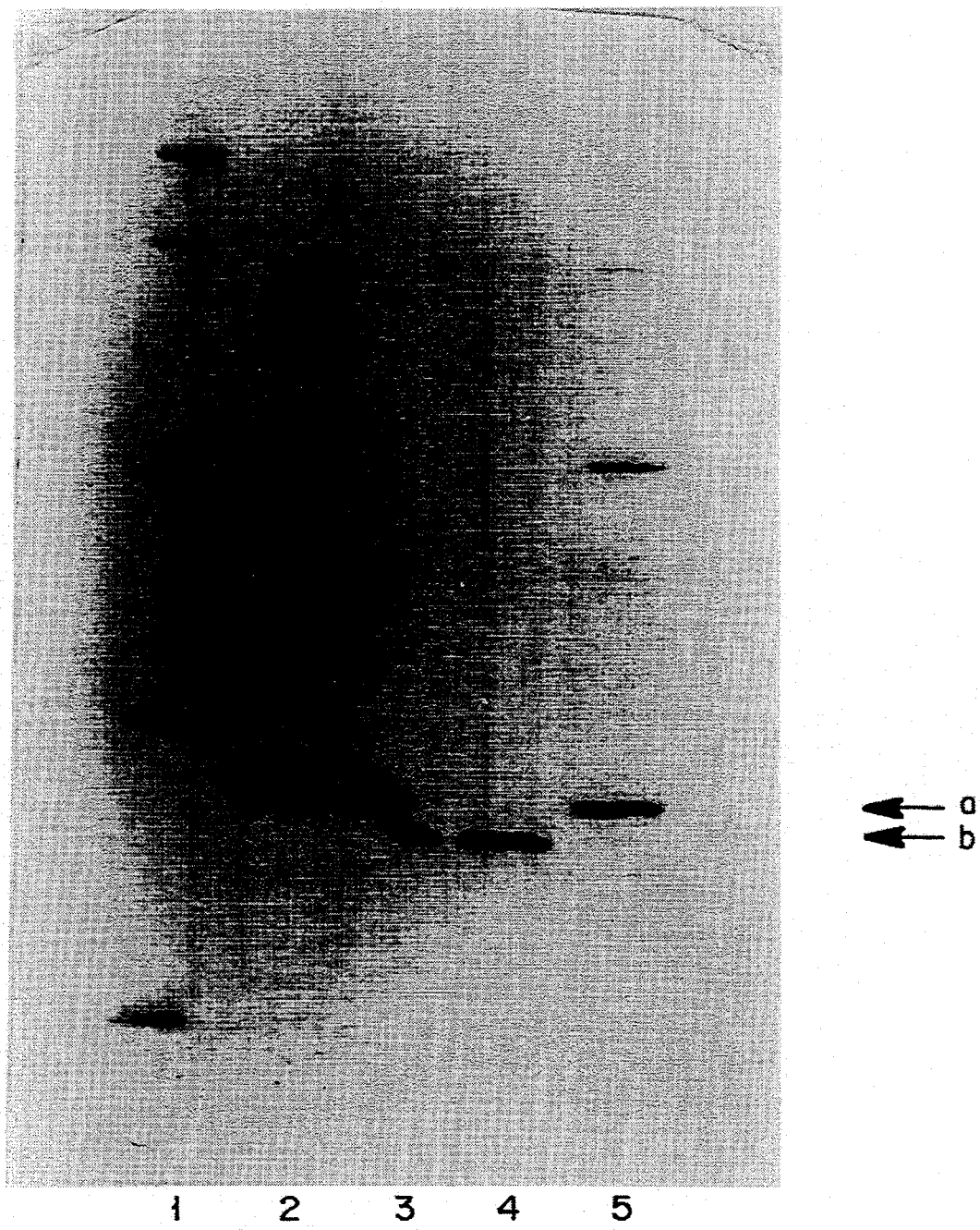
FIG. 13 is a photograph showing the migration pattern of a MAP variant by SDS polyacrylamide gel electrophoresis.

*E. coli* (strain MM294) was transformed by the calcium method using secretion vector pSH7H in which the MAP-H gene was inserted. The resultant transformant was subjected to shaking culture in 2l of L medium (a mixture of 1% bact.trypton, 0.5% bact.yeast extract, 0.5% sodium chloride, and 0.1% glucose) at 30° C. When the absorption of the medium at 550 nm reached 0.8, an equivalent amount of medium preheated to 55° C. was added to the above medium, and the temperature of the total medium was kept at 42° C. The shaking culture was continued at this temperature for 3 hours. Thereafter, ammonium sulfate was added to the medium from which bacteria had been eliminated by centrifugation, so that the concentration of ammonium sulfate was 90% to saturation, and the protein was salted out. This protein was precipitated by centrifugation and was collected. The collected protein was dissolved in 40 ml of A buffer solution (10 mM sodium phosphate buffer solution, pH 6.0), and the A buffer solution was dialyzed. The resultant crude extract was chromatographed on a Carboxymethyl Sepharose column (26 mm in diameter and 40 mm in length) pretreated with the A buffer solution. After the column was sufficiently washed with the A buffer solution, the adsorbed protein was eluted with a sodium chloride solution having a linear gradient of 0M to 0.5M. The MAP-H fractions of the eluted protein were identified and collected by ELISA using an anti-MAP antiserum. The collected proteins were dialyzed using a B buffer solution (10 mM Tris-HCl, pH 8.0) and were chromatographed on a Blue Sepharose column (5 mm in diameter and 50 mm in length) pretreated with B buffer solution. After the column was sufficiently washed with the B buffer solution, the protein was eluted with a sodium chloride solution containing a linear gradient of 0M to 0.2M. MAP-H fractions of the eluted protein were identified and collected by ELISA using an anti-MAP antiserum, and were dialyzed using distilled water, thereby purifying MAP-H. This MAP-H was analyzed by SDS-polyacrylamide gel electrophoresis, and the result is shown in FIG. 13. Referring to FIG. 13, lane 1 represents molecular weight markers, i.e., each band represents 97, 66, 42, 30, and 20 kilodaltons from the top, respectively. Lanes 2 to 4 represent natural MAPs, and lane 5 represents the MAP-H of the present invention. The MAP in lane 2 was reduced with 2-mercaptoethanol immediately before electrophoresis to cleave S-S bonds. As compared with the MAP in lane 4, which was not subjected to reduction, the pattern is found to be changed (a and b). The MAP-H in lane 5 shows the same pattern as the MAP in which the S-S bond is cleaved. Almost no bands representing other impurities are found in the MAP-H migration pattern shown in FIG. 13, and the protein is found to be almost uniform.

M) Inhibition Effect of MAP-H on In Vitro Protein Synthesis

Figure 14:
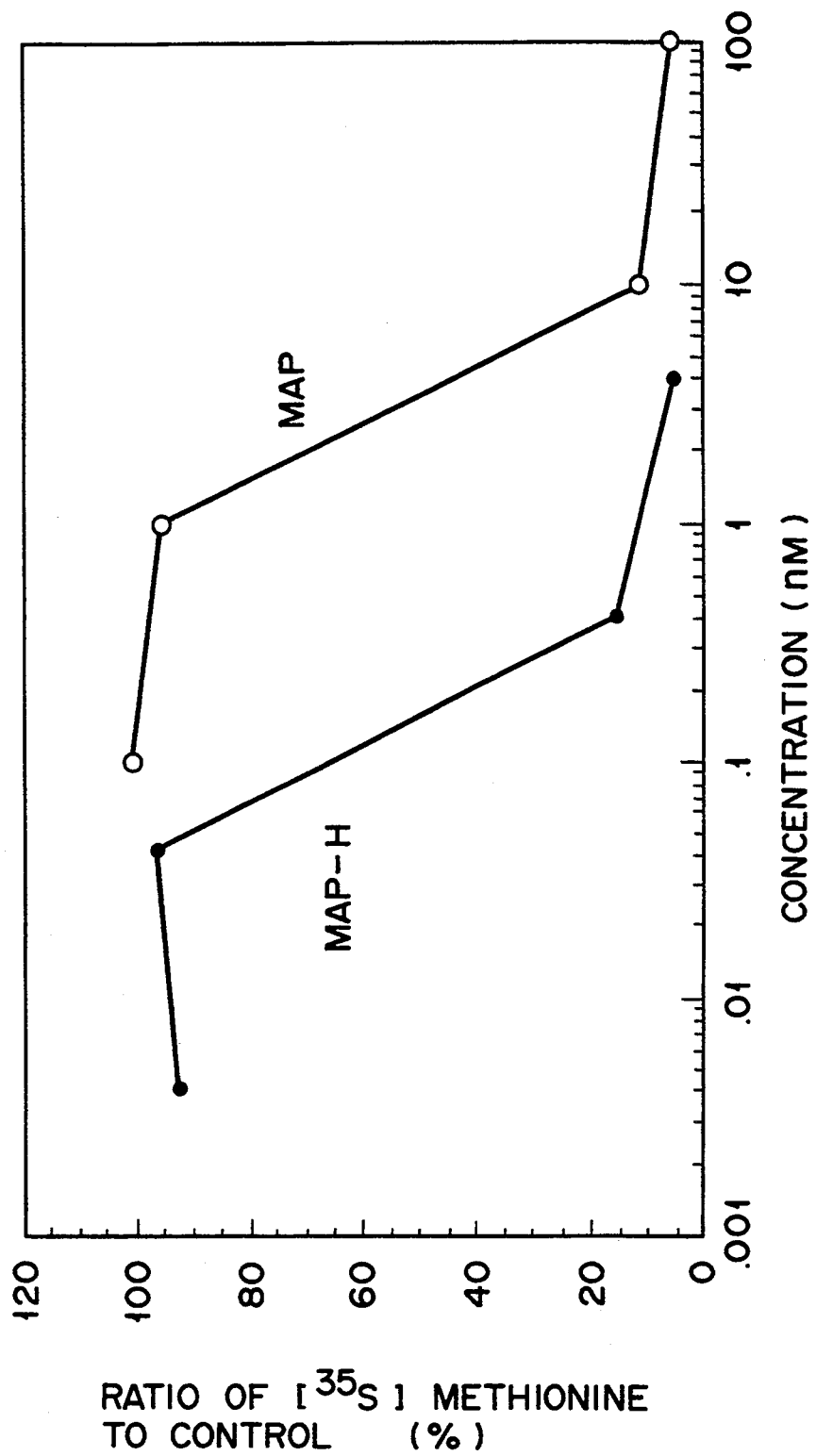
FIG. 14 is a graph showing the protein synthesis inhibition activities of MAP and a MAP variant having no S-S bond in a rabbit reticulocyte system.

Tobacco mosaic virus RNA as mRNA was added to 10 μl of a commercially available rabbit reticulocyte crude extract containing $^{35}$S-methionine and an appropriate amount of MAP or MAP-H, and the resultant mixture was incubated for translation at 30° C. for 30 minutes. Two μl of this reacted solution were placed on filter paper and dried, and this paper was boiled in a 10% trichloroacetic acid solution for 10 minutes. The radioactivity of the radioactive material (polypeptide containing incorporated $^{35}$S) left on the filter paper was measured using a toluene-based scintillator. The radioactivity of a sample not containing the mRNA was defined as 0%, the radioactivity of a sample not containing the MAP or MAP-H was defined as 100% as a control, and the effect of the MAP and MAP-H were determined. The results are shown in FIG. 14. Referring to FIG. 14, the ratio of the amount of incorporated $^{35}$S compared to that of the control is plotted along the ordinate, and the MAP or MAP-H concentration is plotted along the abscissa.

As is apparent from FIG. 14, MAP at about 3.5 mM exhibited a 50% inhibition effect in this system, and MAP-H at about 0.16 nM exhibited a 50% inhibition effect. Thus, the protein synthesis inhibition activity of MAP-H was improved about 22 times compared to that of the natural MAP.

As has bee described above in detail, the MAP variant (MAP-H) having no S-S bond and serving as an antiviral protein according to the present invention exhibits a higher protein synthesis inhibition activity than that of the natural protein, while preserving the advantages of the natural protein. Therefore, the antiviral protein according to the present invention is most promising as a toxic protein used as, e.g., an immunotoxin.

Additional advantages and modifications will readily occur to those skilled in the art. Therefore, the invention in its broader aspects is not limited to the specific details and illustrated examples shown and described herein. Accordingly, various modifications may be made without departing from the spirit or scope of the general inventive concept as defined by the appended claims and their equivalents.

What is claimed is:

1. An antiviral protein having the following amino acid sequence, Seq. ID: No: 8:

```
Ala Pro Thr Leu Glu Thr Ile Ala Ser Leu Asp Leu Asn Asn Pro
 1               5                  10                  15
Thr Thr Tyr Leu Ser Phe Ile Thr Asn Ile Arg Thr Lys Val Ala
                20                  25                  30
Asp Lys Thr Glu Gln Ser Thr Ile Gln Lys Ile Ser Lys Thr Phe
                35                  40                  45
Thr Gln Arg Tyr Ser Tyr Ile Asp Leu Ile Val Ser Ser Thr Gln
                50                  55                  60
Lys Ile Thr Leu Ala Ile Asp Met Ala Asp Leu Tyr Val Leu Gly
                65                  70                  75
Tyr Ser Asp Ile Ala Asn Asn Lys Gly Arg Ala Phe Phe Phe Lys
                80                  85                  90
Asp Val Thr Glu Ala Val Ala Asn Asn Phe Phe Pro Gly Ala Thr
                95                 100                 105
Gly Thr Asn Arg Ile Lys Leu Thr Phe Thr Gly Ser Tyr Gly Asp
               110                 115                 120
Leu Glu Lys Asn Gly Gly Leu Arg Lys Asp Asn Pro Leu Gly Ile
               125                 130                 135
Phe Arg Leu Glu Asn Ser Ile Val Asn Ile Tyr Gly Lys Ala Gly
               140                 145                 150
Asp Val Lys Gln Ala Lys Phe Phe Leu Leu Ala Ile Gln Met
               155                 165                 160
Val Ser Glu Ala Ala Arg Phe Lys Tyr Ile Ser Asp Lys Ile Pro
               170                 175                 180
Ser Glu Lys Tyr Glu Glu Val Thr Val Asp Glu Tyr Met Thr Ala
               185                 190                 195
Leu Glu Asn Asn Trp Ala Lys Leu Ser Thr Ala Val Tyr Asn Ser
               200                 205                 210
Lys Pro Ser Thr Thr Thr Ala Thr Lys Ser Gln Leu Ala Thr Ser
               215                 220                 225
Pro Val Thr Ile Ser Pro Trp Ile Phe Lys Thr Val Glu Glu Ile
               230                 235                 240
Lys Leu Val Met Gly Leu Leu Lys Ser Ser.
               245                 250
```

2. An antiviral protein, wherein said protein is produced by a method comprising culturing *E. coli* harboring plasmid pSH7H, and recovering said antiviral protein.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:

(A) LENGTH: 756 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (A) ORGANISM: Mirabilis jalapa (xi) SEQUENCE DESCRIPTION: SEQ ID NO:1:

| | | | | | | |
|---|---|---|---|---|---|---|
| GCGCCTACTC | TAGAAACCAT | CGCTTCTCTG | GACCTGAACA | ACCCGACCAC | CTACCTGTCT | 60 |
| TTCATAACGA | ATATCCGTAC | GAAAGTCGCA | GACAAAACCG | AACAGTGTAC | CATCCAGAAA | 120 |
| ATCTCTAAAA | CCTTCACCCA | GCGTTACTCT | TACATAGACT | TGATCGTGAG | CTCGACGCAG | 180 |
| AAAATCACCC | TAGCTATCGA | CATGGCTGAC | CTGTACGTTC | TGGGTTACTC | TGACATCGCT | 240 |
| AATAACAAGG | GTCGTGCTTT | CTTCTTCAAA | GACGTGACTG | AGGCTGTTGC | GAACAATTTC | 300 |
| TTCCCGGGAG | CTACAGGTAC | TAATCGTATC | AAATTAACCT | TTACAGGTTC | TTATGGCGAT | 360 |
| CTCGAGAAAA | ACGGCGGACT | ACGTAAGGAC | AATCCCTAG | GTATCTTCCG | TCTGGAAAAC | 420 |
| TCGATAGTTA | ACATTTATGG | CAAAGCTGGT | GACGTTAAAA | AACAGGCTAA | ATTCTTCTTA | 480 |
| CTGGCTATCC | AGATGGTTTC | GGAGGCTGCG | CGCTTTAAGT | ATATCAGTGA | CAAAATCCCG | 540 |
| TCTGAAAAAT | ACGAAGAAGT | TACCGTTGAC | GAATACATGA | CCGCTCTGGA | AAACAACTGG | 600 |
| GCTAAACTGT | CTACGGCCGT | ATACAACTCT | AAGCCTTCTA | CCACCACCGC | TACCAAATGT | 660 |
| CAGCTGGCTA | CCTCTCCGGT | TACCATCTCT | CCGTGGATAT | TCAAAACCGT | CGAGGAAATC | 720 |
| AAACTGGTTA | TGGGTCTGCT | TAAGTCTTCT | TAATAA | | | 756 |

(2) INFORMATION FOR SEQ ID NO:2:

(i) SEQUENCE CHARACTERISTICS:
        (A) LENGTH: 73 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:2:

| | | | | | | |
|---|---|---|---|---|---|---|
| TATGAAAAAG | ACAGCTATCG | CGATTGCAGT | GGCACTGGCT | GGTTTCGCTA | CCGTAGCGCA | 60 |
| GGCCGCGCCT | ACT | | | | | 73 |

(2) INFORMATION FOR SEQ ID NO:3:

(i) SEQUENCE CHARACTERISTICS:
        (A) LENGTH: 56 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:3:

| | | | | | |
|---|---|---|---|---|---|
| AATTCCTGCA | GGTCGACAGG | AAACACATAT | GGCGCCTACT | CTAGAAAATC | GATAAA | 56 |

( 2 ) INFORMATION FOR SEQ ID NO:4:

( i ) SEQUENCE CHARACTERISTICS:
    ( A ) LENGTH: 96 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Mirabilis jalapa ( x i ) SEQUENCE DESCRIPTION: SEQ ID NO:4:

```
CGTACGAAAG  TCGCAGACAA  AACCGAACAG  TCGACCATCC  AGAAAATCTC  TAAAACCTTC      60
ACCCAGCGTT  ACTCTTACAT  AGACTTGATC  GTGAGC                                  96
```

( 2 ) INFORMATION FOR SEQ ID NO:5:

( i ) SEQUENCE CHARACTERISTICS:
    ( A ) LENGTH: 32 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:5:

```
Arg  Thr  Lys  Val  Ala  Asp  Lys  Thr  Glu  Gln  Ser  Thr  Ile  Gln  Lys  Ile
 1              5                        10                        15
Ser  Lys  Thr  Phe  Thr  Gln  Arg  Tyr  Ser  Tyr  Ile  Asp  Leu  Ile  Val  Ser
           20                       25                       30
```

( 2 ) INFORMATION FOR SEQ ID NO:6:

( i ) SEQUENCE CHARACTERISTICS:
    ( A ) LENGTH: 81 base pairs
    ( B ) TYPE: nucleic acid
    ( C ) STRANDEDNESS: double
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Mirabilis jalapa ( x i ) SEQUENCE DESCRIPTION: SEQ ID NO:6:

```
AGCTTGGCGG  CCGTATACAA  CTCTAAGCCT  TCTACCACCA  CCGCTACCAA  ATCTCAACTG      60
GCTACCTCTC  CGGTTACCAA  G                                                   81
```

( 2 ) INFORMATION FOR SEQ ID NO:7:

( i ) SEQUENCE CHARACTERISTICS:
    ( A ) LENGTH: 23 amino acids
    ( B ) TYPE: amino acid
    ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:7:

```
Ala Val Tyr Asn Ser Lys Pro Ser Thr Thr Thr Ala Thr Lys Ser Gln
1               5                   10                  15
Leu Ala Thr Ser Pro Val Thr
            20
```

( 2 ) INFORMATION FOR SEQ ID NO:8:

( i ) SEQUENCE CHARACTERISTICS:
        ( A ) LENGTH: 250 amino acids
        ( B ) TYPE: amino acid
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( v i ) ORIGINAL SOURCE:
        ( A ) ORGANISM: Mirabilis jalapa ( x i ) SEQUENCE DESCRIPTION: SEQ ID NO:8:

```
Ala Pro Thr Leu Glu Thr Ile Ala Ser Leu Asp Leu Asn Asn Pro Thr
1               5                   10                  15
Thr Tyr Leu Ser Phe Ile Thr Asn Ile Arg Thr Lys Val Ala Asp Lys
                20                  25                  30
Thr Glu Gln Ser Thr Ile Gln Lys Ile Ser Lys Thr Phe Thr Gln Arg
            35                  40                  45
Tyr Ser Tyr Ile Asp Leu Ile Val Ser Ser Thr Gln Lys Ile Thr Leu
    50                  55                  60
Ala Ile Asp Met Ala Asp Leu Tyr Val Leu Gly Tyr Ser Asp Ile Ala
65                  70                  75                  80
Asn Asn Lys Gly Arg Ala Phe Phe Phe Lys Asp Val Thr Glu Ala Val
                85                  90                  95
Ala Asn Asn Phe Phe Pro Gly Ala Thr Gly Thr Asn Arg Ile Lys Leu
                100                 105                 110
Thr Phe Thr Gly Ser Tyr Gly Asp Leu Glu Lys Asn Gly Gly Leu Arg
            115                 120                 125
Lys Asp Asn Pro Leu Gly Ile Phe Arg Leu Glu Asn Ser Ile Val Asn
    130                 135                 140
Ile Tyr Gly Lys Ala Gly Asp Val Lys Lys Gln Ala Lys Phe Phe Leu
145                 150                 155                 160
Leu Ala Ile Gln Met Val Ser Glu Ala Ala Arg Phe Lys Tyr Ile Ser
                165                 170                 175
Asp Lys Ile Pro Ser Glu Lys Tyr Glu Glu Val Thr Val Asp Glu Tyr
                180                 185                 190
Met Thr Ala Leu Glu Asn Asn Trp Ala Lys Leu Ser Thr Ala Val Tyr
            195                 200                 205
Asn Ser Lys Pro Ser Thr Thr Thr Ala Thr Lys Ser Gln Leu Ala Thr
    210                 215                 220
Ser Pro Val Thr Ile Ser Pro Trp Ile Phe Lys Thr Val Glu Glu Ile
225                 230                 235                 240
Lys Leu Val Met Gly Leu Leu Lys Ser Ser
                245                 250
```

( 2 ) INFORMATION FOR SEQ ID NO:9:

(i) SEQUENCE CHARACTERISTICS:
  (A) LENGTH: 762 base pairs
  (B) TYPE: nucleic acid
  (C) STRANDEDNESS: double
  (D) TOPOLOGY: linear (ii) MOLECULE TYPE: DNA (genomic)

(iii) HYPOTHETICAL: NO (iv) ANTI-SENSE: NO (v) ORIGINAL SOURCE:
  (A) ORGANISM: Mirabilis jalapa (xi) SEQUENCE DESCRIPTION: SEQ ID NO:9:

```
GCGCCTACTC TAGAAACCAT CGCTTCTCTG GACCTGAACA ACCCGACCAC CTACCTGTCT    60
TTCATAACGA ATATCCGTAC GAAAGTCGCA GACAAAACCG AACAGTCGAC CATCCAGAAA   120
ATCTCTAAAA CCTTCACCCA GCGTTACTCT TACATAGACT TGATCGTGAG CTCGACGCAG   180
AAAATCACCC TAGCTATCGA CATGGCTGAC CTGTACGTTC TGGGTTACTC TGACATCGCT   240
AATAACAAGG GTCGTGCTTT CTTCTTCAAA GACGTGACTG AGGCTGTTGC GAACAATTTC   300
TTCCCGGGAG CTACAGGTAC TAATCGTATC AAATTAACCT TTACAGGTTC TTATGGCGAT   360
CTCGAGAAAA ACGGCGGACT ACGTAAGGAC AATCCCCTAG GTATCTTCCG TCTGGAAAAC   420
TCGATAGTTA ACATTTATGG CAAAGCTGGT GACGTTAAAA AACAGGCTAA ATTCTTCTTA   480
CTGGCTATCC AGATGGTTTC GGAGGCTGCG CGCTTTAAGT ATATCAGTGA CAAAATCCCG   540
TCTGAAAAAT ACGAAGAAGT TACCGTTGAC GAATACATGA CCGCTCTGGA AAACAACTGG   600
GCTAAACTGT CTACGGCCGT ATACAACTCT AAGCCTTCTA CCACCACCGC TACCAAATCT   660
CAACTGGCTA CCTCTCCGGT TACCATCTCT CCGTGGATAT TCAAAACCGT CGAGGAAATC   720
AAACTGGTTA TGGGTCTGCT TAAGTCTTCT TAATAAATCG AT                      762
```